US006682656B2

(12) United States Patent
Rothman et al.

(10) Patent No.: US 6,682,656 B2
(45) Date of Patent: Jan. 27, 2004

(54) BIOLOGICAL FLUID TREATMENT SYSTEM AND METHOD

(75) Inventors: Isaac Rothman, Brooklyn, NY (US);
Thomas Gsell, Glen Head, NY (US);
Gerard R. DelGiacco, Yonkers, NY (US); Richard Salinaro, Hastings-on-Hudson, NY (US); Randy Garcez, Yorba Linda, CA (US)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 10/287,497

(22) Filed: Nov. 5, 2002

(65) Prior Publication Data

US 2003/0075516 A1 Apr. 24, 2003

Related U.S. Application Data

(63) Continuation of application No. 09/600,752, filed as application No. PCT/US99/00863 on Jan. 15, 1999, now Pat. No. 6,497,823.
(60) Provisional application No. 60/072,315, filed on Jan. 23, 1998, and provisional application No. 60/072,973, filed on Jan. 29, 1998.

(51) Int. Cl.[7] .......................... B01D 37/00; B01D 35/00
(52) U.S. Cl. .................. 210/767; 210/435; 210/488; 210/489; 210/490; 210/504; 210/506; 604/406; 604/408

(58) Field of Search ................... 210/488, 489, 210/490, 496, 504, 506, 508, 645, 650, 767, 651, 782, 787, 789, 806, 435; 604/408, 410, 406

(56) References Cited

U.S. PATENT DOCUMENTS

| | | | |
|---|---|---|---|
| 4,235,233 A | | 11/1980 | Mouwen |
| 4,466,888 A | * | 8/1984 | Verkaart ................ 210/232 |
| 4,734,269 A | * | 3/1988 | Clarke et al. ............ 96/156 |
| 4,880,548 A | | 11/1989 | Pall et al. |
| 4,978,578 A | * | 12/1990 | Kanno et al. ............ 428/412 |
| 5,100,564 A | * | 3/1992 | Pall et al. ............... 210/782 |
| 5,217,627 A | | 6/1993 | Pall et al. |
| 5,421,824 A | * | 6/1995 | Clement et al. ............ 604/29 |
| 5,695,489 A | | 12/1997 | Jupuntich |
| 5,928,516 A | * | 7/1999 | Hopkins et al. ........... 210/636 |
| 6,099,734 A | * | 8/2000 | Boggs et al. .............. 210/650 |

FOREIGN PATENT DOCUMENTS

| | | | |
|---|---|---|---|
| EP | 0 230 247 A | | 7/1987 |
| WO | WO 91/04088 | * | 4/1991 |
| WO | 93 04763 A | | 3/1993 |

* cited by examiner

*Primary Examiner*—John Kim
(74) *Attorney, Agent, or Firm*—Leydig, Voit & Mayer, Ltd.

(57) ABSTRACT

Devices, systems and methods for treating a biological fluid are provided comprising placing the fluid in contact with a complement filter capable of depleting at least one complement fragment from the fluid while at least one component of the biological fluid is being stored.

24 Claims, 2 Drawing Sheets

BIOLOGICAL FLUID TREATMENT SYSTEM AND METHOD

This application is a continuation of U.S. application Ser. No. 09/600,752, filed Jul. 21, 2000, U.S. Pat. No. 6,497,823, which is a 371 of International Application No. PCT/US99/00863, filed Jan. 15, 1999. This application claims the benefit of U.S. provisional patent applications 60/072,315, filed Jan. 23, 1998, and 60/072,973, filed Jan. 29, 1998, which are incorporated by reference in their entireties.

TECHNICAL FIELD

This invention relates to treating biological fluid, and particularly relates to removing at least one complement fragment from blood components, especially platelet concentrate or apheresis platelets, during storage.

BACKGROUND OF THE INVENTION

The complement system acts on its own and in cooperation with antibodies in defending vertebrates against infection. The complement system is composed of a series of plasma-borne blood proteins (proenzymes) that are sequentially activated in a series of reactions. The proteins are activated in cascade fashion, i.e., the output of one reaction is the input for the next. The cascade ultimately generates a terminal five-protein membrane attack complex (MAC, C5b-9), whose physiological function is protection of the host from invading microorganisms. The MAC causes lysis of the microorganisms.

While the complement system is generally beneficial in protecting the host, the presence of the various activated or activatable blood proteins (and fragments thereof) can be undesirable, particularly when these proteins and/or fragments are present in blood or blood components used for transfusion. For example, transfusing activated complement into a patient can cause adverse affects such as anaphylactoid reactions, platelet aggregation, and/or immune suppression. The problem can be magnified when transfusing stored blood or blood components, since the proteins can be activated while processing the blood components and/or while storing the components, e.g., due to contact between the plasma-borne proteins and the surfaces of the plastic blood bag and/or the blood bag tubing. Activation can lead to the administration of biologically active complement fragments such as C3a and its metabolite, C3a des $Arg^{77}$.

Accordingly, there is a need in the art for a device for use with blood and blood components that removes at least one complement fragment. Additionally, since activated complement can continue to accumulate during storage, there is an unaddressed need in the art for a device that removes at least one complement fragment from the desired blood component(s) during the storage period without requiring additional processing steps that could lead to further complement activation.

The present invention provides for ameliorating at least some of the disadvantages of the prior art. These and other advantages of the present invention will be apparent from the description as set forth below.

SUMMARY OF THE INVENTION

In accordance with the present invention, a biological fluid is placed in contact with a complement filter, wherein the filter depletes complement from the fluid. In a more preferred embodiment, the filter is capable of retaining complement without substantially retaining desirable components of the biological fluid.

Preferably, the present invention provides for collecting a biological fluid in a container including the complement filter, and storing the fluid in the container so that a significant amount of the complement produced during storage is captured or retained by the filter. Thus, the filter can provide a complement "sink." In a more preferred embodiment, the movement of biological fluid in the bag, e.g., as the bag is handled during handling and/or storage protocols, exposes more of the fluid to the complement filter, thus continuing to remove or retain complement as it is produced.

Systems, methods and devices according to the present invention are compatible with a wide variety of biological fluid treatment protocols, and, in preferred embodiments, require little or no modification of existing biological fluid handling steps or procedures. Thus, another advantage of one embodiment of the present invention is that there is no need to re-train the technicians carrying out the biological fluid processing protocol.

The following definitions are used in accordance with the invention:

(A) Complement. As used herein, the term "complement" includes at least one of a complement protein, complement component (e.g., C1 through C9), complement fragment, biologically active fragment of a component (and metabolite of the fragment), complement factor (e.g., factor B and factor D), complement subcomponent, and complement complex (e.g., $C\overline{567}1$). Exemplary biologically active fragments and metabolites thereof include C3a, C3a des $Arg^{77}$, C4a, C4a des Arg, C5a, and C5a des Arg.

(B) Biological Fluid. A biological fluid includes any treated or untreated fluid (including a suspension) associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), apheresed platelets, platelet-rich plasma (PRP), platelet-poor plasma (PPP), platelet-free plasma, plasma, serum, fresh frozen plasma (FFP), components obtained from plasma, packed red cells (PRC), buffy coat (BC); blood products derived from blood or a blood component or derived from bone marrow; red cells separated from plasma and resuspended in physiological fluid; and platelets separated from plasma and resuspended in physiological fluid. The biological fluid may have been treated to remove some of the leukocytes before being processed according to the invention. As used herein, blood product or biological fluid refers to the components described above, and to similar blood products or biological fluids obtained by other means and with similar properties.

A "unit" is the quantity of biological fluid from a donor or derived from one unit of whole blood. It may also refer to the quantity drawn during a single donation, e.g., during apheresis. Typically, the volume of a unit varies, the amount differing from patient to patient and from donation to donation. Multiple units of some blood components, particularly whole blood derived platelets and buffy coat, may be pooled or combined, typically by combining four or more units.

(C) Complement Filter. The complement filter separates complement from the biological fluid, e.g., it captures, binds, or retains complement (defined above). Thus, the complement filter can be used to provide a complement-depleted biological fluid. For example, the filter can remove or retain at least one complement fragment, e.g., biologically active complement fragments such as at least one of C3a and C5a. In a preferred embodiment, the complement filter removes C3a. In some embodiments, the complement filter can also suppress complement activation.

Preferably, the filter removes or retains complement, more preferably, C3a, without adversely affecting, or without significantly adversely affecting, the clinical effects of desirable biological fluid components such as plasma, platelets, and/or red blood cells. More preferably, the filter removes or retains C3a without significantly reducing the recovery of the desirable biological fluid component(s). In some embodiments, the complement filter also removes or retains undesirable material such as interleukin 8 (IL 8) and/or RANTES.

In an embodiment, the complement filter comprises at least one porous substrate of any suitable nature, e.g., a fibrous web, a membrane, combinations thereof, and the like. The porous substrate can have any suitable physical dimensions and typically will be in sheet form having two opposing sides (e.g., a first side and an opposing second side) with a central portion therebetween, wherein the pores in the porous substrate will generally enable fluid communication between the first and second sides of the porous substrate. Preferably, the complement filter comprises at least one membrane, more preferably a microporous membrane, through which at least a portion of the plasma component of a biological fluid (e.g., a portion of the plasma present in blood, or the plasma suspending other blood components such as red blood cells and/or platelets) passes. The membrane has two opposing sides (e.g., a first side and an opposing second side, in relation to a biological fluid to be treated wherein at least a portion of the plasma component is passed through the membrane), with a central portion therebetween. The pores in the membrane generally enable fluid communication between the two opposing sides (e.g., between the first and second sides) of the membrane.

The complement filter can have any suitable pore rating (e.g., ability to remove particles of a given size to a specified degree, as evidenced, for example, by bubble point).

The filter can include additional elements or structures, which can also be membranes, or other media, including porous media. For example, in some embodiments, the filter can include additional components that have different structures and/or functions. Illustratively, the filter can also include at least one additional structure such as a fibrous medium (e.g., a nonwoven web and/or a woven web), a mesh and/or a screen.

SPECIFIC DESCRIPTION OF THE INVENTION

In accordance with a method provided by the instant invention, a biological fluid is placed in contact with a complement filter capable of depleting complement from the fluid, and complement is depleted from the biological fluid. Complement can be removed during the initial and/or the subsequent contact between the biological fluid and the filter. Some embodiments of the method include placing the biological fluid in contact with the complement filter and removing complement from the biological fluid without passing the fluid along a substantially defined fluid flow path through the complement filter medium.

According to an embodiment of the invention, a method for processing a biological fluid is provided comprising collecting a biological fluid in a container including a complement filter capable of depleting complement from the biological fluid, wherein at least a portion of the fluid contacts the complement filter while the fluid is being collected in the container. In a more preferred embodiment of the invention, the biological fluid, or at least one component thereof, is stored for at least 24 hours in the container having the complement filter therein, and the biological fluid, or at least a portion thereof, is repeatedly or continuously placed in contact with the filter during the storage period, and a substantial amount of the complement produced during storage is removed from the biological fluid.

In accordance with an embodiment of the invention, a complement filter is provided, the filter comprising a surface-modified membrane, wherein the filter is capable of removing complement from a biological fluid. In a more preferred embodiment, the complement filter comprises a porous polymeric surface-modified membrane having a negative zeta potential at physiological pH.

In an embodiment, the present invention provides a device for treating a biological fluid comprising a container suitable for containing the biological fluid, and a complement filter disposed in the container. In some embodiments, the complement filter is disposed within the container to contact the fluid as it is collected in the container without providing a substantially defined fluid flow path through the complement filter medium.

Each of the components of the invention will now be described in more detail below, wherein like components have like reference numbers.

Figure 1:
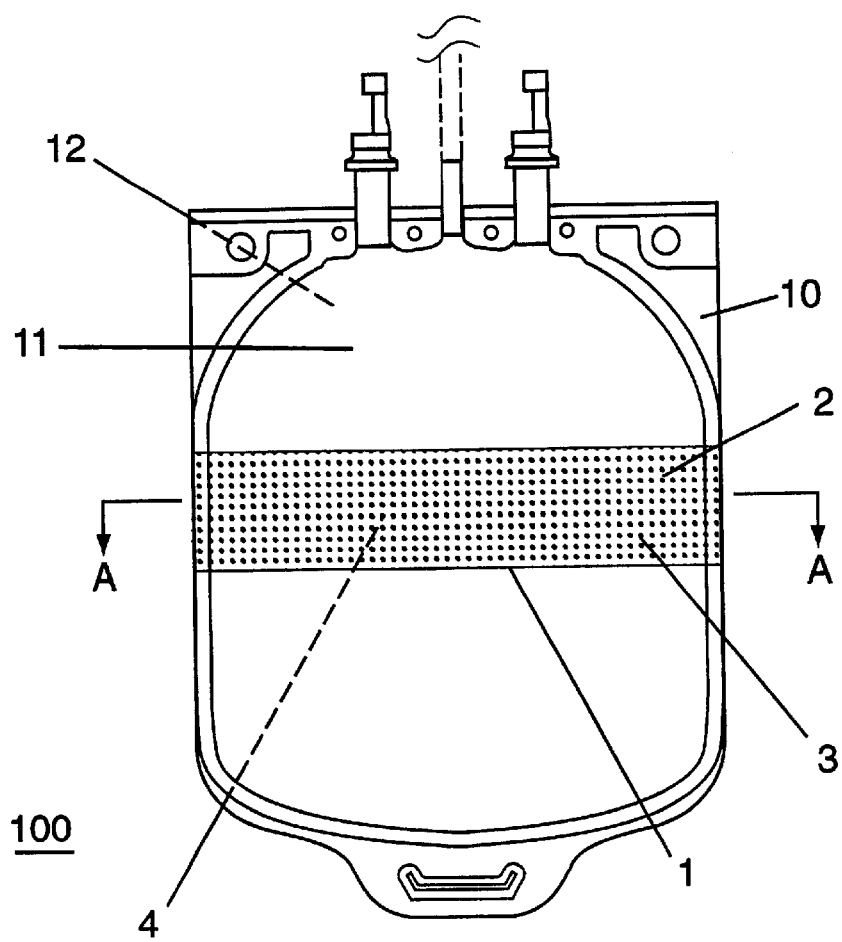
FIG. 1 shows a perspective view of an embodiment of the invention, illustrating a blood bag including a complement filter, wherein the filter extends from one side seal of the bag to the other side seal.

FIG. 1 illustrates one embodiment of the invention, and shows a biological fluid treatment device 100, comprising a complement filter 1 disposed in a container 10 such as a flexible blood bag that has a defined inner volume for receiving fluid. In this illustrated embodiment, the complement filter 1 comprises a porous membrane 2, having a first surface 3 and a second surface 4.

Figure 2:
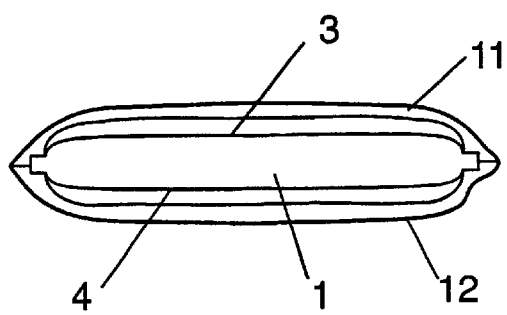
FIG. 2 is a cross-sectional view of FIG. 1 along line A—A.

The illustrated container 10 comprises a first side or front side 11 and a second side or back side 12, wherein the sides are sealed together, and the inner surfaces of the front and back sides form the inner walls of the container. The cross-sectional view according to the embodiment illustrated in FIG. 2 shows the complement filter 1 secured in the container 10, wherein portions of the filter 1 are retained in the side seals between the front and back sides 11 and 12 of the container.

Figure 3:
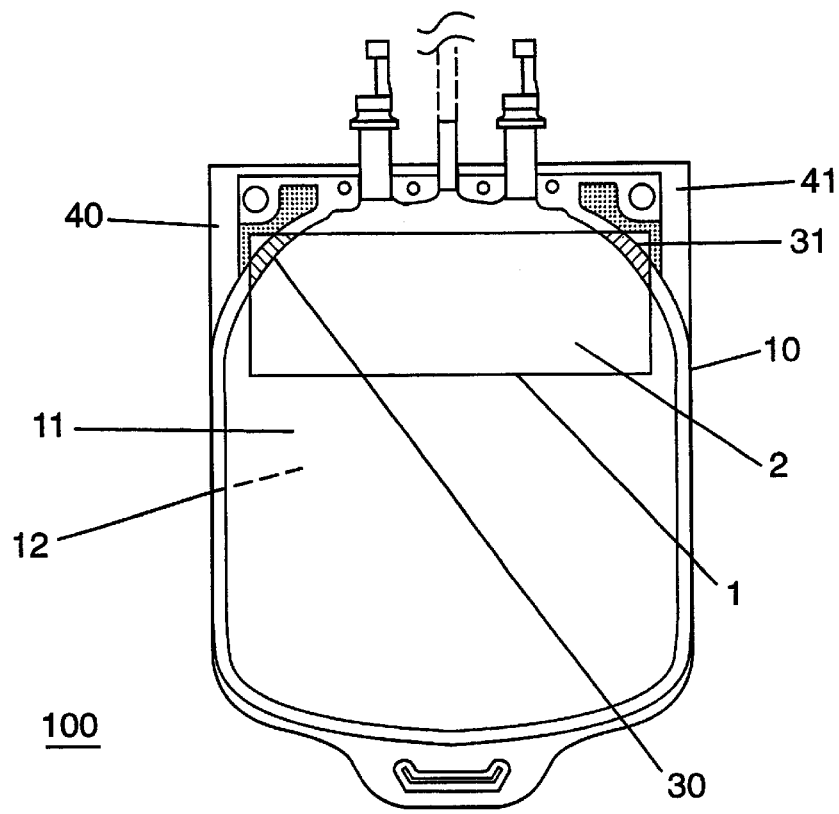
FIG. 3 shows a perspective view of another embodiment of the invention, illustrating a blood bag including a complement filter, wherein the filter is secured in an end seal of the bag.

FIG. 3 illustrates another exemplary embodiment, wherein a portion of the filter 1 is secured in the top end seal between the front and back sides 11 and 12 of the container. In this illustrated embodiment, the filter 1 is also secured between the front and back sides 11 and 12 of the container at portions 30 and 31. FIG. 3 also shows additional seals between the front and back sides of the container at portions 40 and 41, wherein these seals do not contact the filter.

In another exemplary embodiment, the filter is not retained in the seal between the front and back sides of the container. For example, at least a portion of the filter can be secured to an inner wall of the container. Illustratively, in accordance with the embodiment of the device 100 shown in FIG. 4, the filter 1 is secured to the inner surface of side 11 of container 10 at portions 20 and 21.

In yet another embodiment (not shown) the filter is movable within the interior volume of the container. For example, if desired, the filter is neither attached nor secured to the container. Of course, the filter can be tethered in the container.

In accordance with the invention, the complement filter 1 is capable of depleting complement from a biological fluid upon initial and/or subsequent contact between the fluid and the filter. Typically, the device 100 includes complement filter 1 disposed in the container 10 so that at least a portion of the fluid contacts the filter as the fluid is being collected in the container. For example, the filter 1 can be disposed in the container 10 to allow at least some of the biological fluid to pass tangentially across the first surface 3 and/or the second surface 4 of the membrane 2, thus removing some amount of complement as the fluid is collected in the container. In some embodiments, as fluid passes tangentially across a membrane surface, at least a portion of the plasma component of the biological fluid passes through the membrane, i.e., the plasma passes from one surface of the membrane and through the central portion to the other surface of the membrane.

Figure 4:
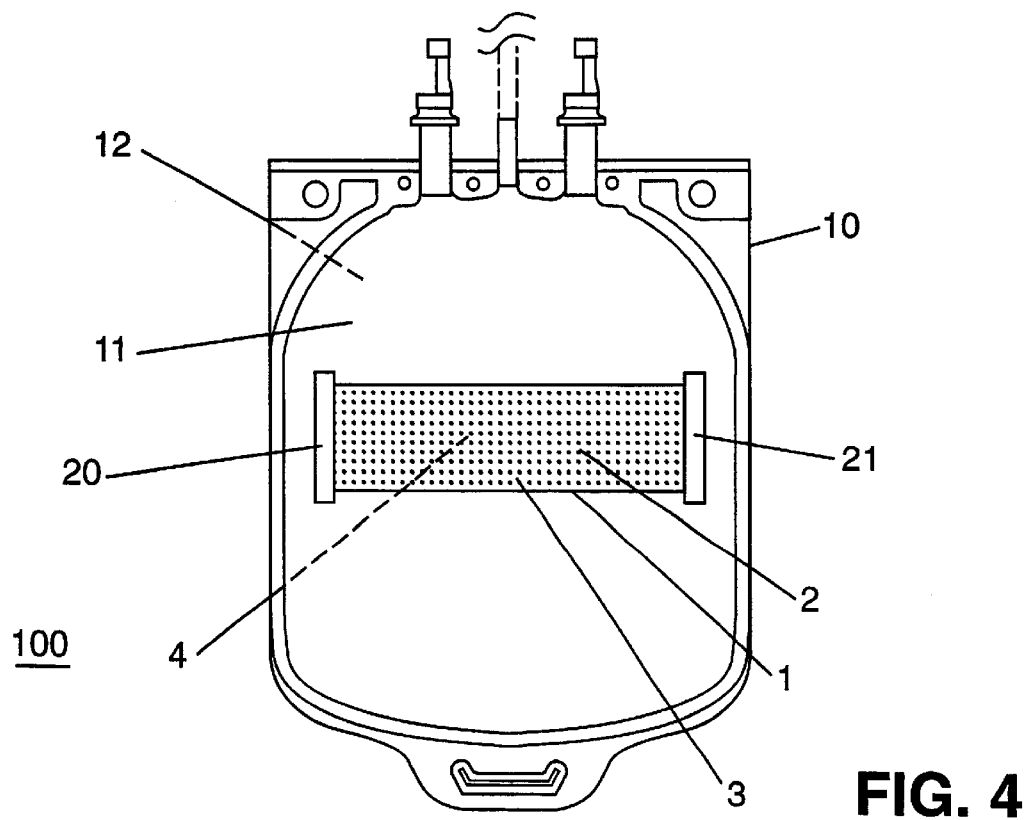
FIG. 4 shows a perspective view of another embodiment of the invention, illustrating a blood bag including a complement filter.

In typical embodiments according to FIGS. 1, 3, and 4, the device 100 does not direct all the biological fluid through the membrane 2 as the fluid is collected in the container 10. Of course, if desired, the device 100 can be configured to provide a substantially defined fluid flow path therethrough, e.g., to ensure that substantially all of the biological fluid passes through the membrane 2 while the fluid is collected in the container 10.

Preferably, the biological fluid, or at least one component thereof, is stored in the container 10, and the filter 1 is disposed in the container so that the biological fluid, or at least a portion thereof, is repeatedly or continuously placed in contact with the filter 1 during the storage period. In this preferred embodiment, a substantial amount of complement that is produced during the storage period is retained or captured by the filter. Accordingly, the biological fluid can be passed from the container after the storage period without passing a substantial amount of complement along with the fluid.

A variety of materials are suitable for producing the complement filter 1, and the filter can be homogenous or comprised of a combination of materials. Preferably, the porous substrate comprises (and can consist essentially, or even consists entirely, of) a polymeric material. For example, the membrane 2 is typically a polymeric material such as, but not limited to, nylon, polyethylene, polypropylene, polyurethane, polyphenylene sulfide, syndiotactic polystyrene, polyester PET (polyethylene terephthalate) and polyester PBT (polybutylene terephthalate).

If desired, the membrane 2 can be surface modified, e.g., the membrane may be exposed to radiation grafting and/or gas plasma treatment. For example, the membrane can be surface modified to render it hydrophilic (i.e., having a critical wetting surface tension (CWST) of at least about 72 dynes/cm (72 mN/m) as determined by the CWST test disclosed in U.S. Pat. No. 4,880,548. Alternatively, or additionally, the membrane can be surface modified to provide, for example, an increased and/or a longer lasting capability to capture or retain complement upon contact with the fluid.

For example, the membrane 2 is preferably surface modified to render at least a portion of a surface anionic, e.g., to provide a surface having a negative zeta potential at physiological pH (about 7 to about 7.4). One procedure for determining zeta potential is disclosed in U.S. Pat. No. 5,217,627. More preferably, the membrane 2 is surface modified to render the first surface 3 and second surface 4 anionic. Such surface modification in accordance with the invention can be carried out in any suitable manner and is preferably accomplished by graft polymerizing a suitable monomer onto the surface of the membrane. Preferred examples of such monomers include those wherein the non-reactive end of the molecule contains at least one group having anionic character, such as one or more sulfonic acid groups or carboxyl or carboxylic groups, e.g., acrylic or methacrylic monomers having acrylic functional groups, such as, for example, acrylic acid and methacrylic acid. Other suitable monomers include unsaturated mono, or di-carboxylic acids, for example, itaconic acid, derivatives of anhydrides such as maleic anhydride, or sulfonic acid and derivatives thereof.

While the mechanism of complement removal is not well understood, it may be removed by adsorption, e.g., via ionic interaction between the complement and the surface of the filter. Illustratively, at physiological pH, C3a has a cationic character, and can complex with anionic groups on or at the surface of the filter.

While graft polymerization to provide an anionic character to the surface of the membrane can be carried out in the absence of crosslinking agents, it is preferred that such crosslinking agents be used, particularly when the aforementioned acrylate monomers are graft polymerized onto the surface of the membrane. Any suitable crosslinking agent can be used in the context of the present invention. Suitable crosslinking agents include multifunctional esters, e.g., di- or poly-acrylates and methacrylates of diols and polyols, particularly linear or branched aliphatic diols such as ethylene glycol, 1,2-propylene glycol, diethylene glycol, dipentylene glycol, polyethylene glycol, polypropylene glycol, polytetramethylene-oxide glycol, and poly(ethylene oxide-copropylene-oxide) glycol, as well as triol acrylates such as trimethylolpropane triacrylate. Examples of other crosslinking monomers that may be used in the instant invention include allyls, maleimides, unsaturated dicarboxylic acids, aromatic vinyl compounds, polybutadienes, and trimellitic acid esters.

Ethylene glycol dimethacrylates including one, preferably, two or more, ethylene oxide repeating units are preferred crosslinking agents in the context of the present invention. Diethylene glycol dimethacrylate (DEGDMA) and polyethylene glycol dimethacrylate (PEGDMA) are two examples of preferred crosslinking agents.

In a preferred embodiment, the pore structure (e.g., the pore rating) of the complement filter is such that the desired cellular components of the biological fluid, e.g., red blood cells and/or platelets, will be prevented from entering the interior portion of the filter medium or media. In some embodiments, preventing desired cellular components from entering the interior of the filter can be advantageous, e.g., in reducing the number of cells that are retained in the interior of the filter. For example, in those embodiments wherein the biological fluid to be processed includes platelets, e.g., wherein the biological fluid to be eventually transfused is platelet concentrate or aphereseed platelets, the membrane preferably has a pore size of about 2 micrometers or less, that prevents many of the platelets from entering the interior of the membrane. In another embodiment, the membrane has a pore size of about 1 micrometer or less.

The area of the filter, and the arrangement of the filter in the container may vary according to, for example, the biological fluid being processed, the type and/or size of the container, and the processing protocol.

With respect to the area, in one embodiment, the membrane has an area of, for example, at least about 2 $cm^2$, preferably, at least about 4 $cm^2$. In a typical embodiment, the membrane has an area of about 120 $cm^2$ or less, preferably, about 100 $cm^2$ or less. For example, in some embodiments, the membrane has an area in the range of from about 6 $cm^2$ to about 75 cm.

The filter 1 can be arranged in the container 10 in a variety of configurations. Typically, the filter has a substantially planar configuration, with the major surfaces of the filter substantially parallel to the major inner walls of the empty container. If desired, the filter can extend from within or near at least one end and/or side seal of the container to within or near another end and/or side seal of the container. For example, FIG. 1 shows an embodiment wherein the filter 1 extends from within one side seal of the container 10 to the other side seal. Alternatively, the filter need not extend to either or both side seals and/or end seals. For example, FIG. 3 shows an embodiment wherein the filter 1 is retained within one end seal of the container 10, and does not extend to another seal. FIG. 4 shows another illustrative embodiment wherein the filter 1 is not retained within a side or an end seal of the container, and does not extend to either end or side seal of the container 10.

Additionally, or alternatively, the filter 1 can extend from one end of the container (e.g., the "top" of the container, including a port allowing fluid to enter the container) to the other end of the container (e.g., the "bottom" of the container, opposite the end where fluid enters the container). Typically, however, as shown in FIG. 1 for example, the filter 1 does not extend to the top and bottom of the container. If desired, the filter can be disposed more toward the center of the container, or more toward the bottom or the top of the container.

With respect to the fluid handling protocol, those embodiments including more movement of the container of fluid, for example, centrifuging, rocking, rotating and/or inverting the container, may allow more of the surface area of the filter to be contacted by the fluid. Additionally, in accordance with some of those embodiments that do not include centrifuging the container, e.g., wherein the container is utilized for apheresed platelets, the filter can be disposed more toward the bottom of the container. Since the container is not centrifuged, the platelets will not be centrifugally forced against the filter during processing. Alternatively, in accordance with some of the embodiments that include centrifuging the container, e.g., wherein the container receives platelet-rich-plasma (PRP), and is then centrifuged to provide platelet concentrate (PC), the filter can be disposed more toward the top of the container.

A variety of containers 10 are suitable for carrying out the invention, and are already known in the art. A preferred container for collecting biological fluid comprises a sealed container equipped with access conduits, and access ports. In an embodiment, the container is suitable for use in an apheresis system.

The container may be constructed of any material compatible with biological fluids. The container can be formed as is known in the art. Illustratively, in some embodiments wherein the container is a flexible container such as a blood bag, the container can be formed, for example, from a single sheet that is folded over and sealed, or from separate sheets that are sealed together, or from blow mold techniques. In some embodiments, the container is capable of withstanding centrifugation. Illustratively, the container may be a flexible container such as a blood collection or satellite bag, which is typically made from plasticized PVC, e.g., PVC plasticized with dioctylphthalate, diethylhexylphthalate, trioctyltrimellitate, or citrate. The bag may also be formed from, for example, polyolefin, polyurethane, polyester, or polycarbonate. In other embodiments, the container comprises a rigid or substantially rigid container, e.g., as used to provide a drip chamber or a bubble trap.

In some embodiments, the filter can be moved from one portion of the interior of the container to another portion while biological fluid is present in the container. For example, the filter can be capable of freely moving (e.g., floating) in the container of biological fluid, with or without a tether between the filter and the container.

In those embodiments wherein the filter 1 is secured to the container 10, the filter can be secured in any suitable manner. For example, at least one portion of the filter, e.g., an end or edge of the filter, can be sealed between the front and back sides of the container. Alternatively, or additionally, at least one portion of the filter can be secured elsewhere, e.g., to an inner wall of the container.

Illustratively, the sides of the container can be sealed, with an end of the filter therebetween, and/or a portion of the filter can be secured to the inner walls of the container, utilizing an adhesive, a solvent, radio frequency sealing and/or heat sealing. If desired, the container can include any number of seals, without or without a portion of the filter secured or retained therein.

The present invention is compatible with a variety of biological fluid processing systems, devices and protocols. For example, the present invention can be used in open or closed systems, and can be used after the biological fluid has been donated, or while the donation process is on-going, e.g., the present invention can be included in an apheresis blood bag system. Embodiments of the present invention can also be used while biological fluid is administered, e.g., the complement filter can be included in a transfusion administration set.

In accordance with the method provided by the invention, a biological fluid is placed in contact with a complement filter 1, and the complement filter removes or depletes complement from the fluid. Complement can be removed as the biological fluid initially contacts the filter, and/or as the biological fluid, or at least one component thereof, contacts the filter over a period of time, e.g., during storage.

In an embodiment of a method in accordance with the present invention, a biological fluid is passed into a device 100 comprising container 10 that includes the complement filter 1 disposed therein. Typically, as the biological fluid is collected in container 10, at least a portion of the biological fluid contacts the filter 1. In one of the embodiments wherein the filter is not freely movable in the container, as the biological fluid is collected, at least some of the biological fluid passes tangentially across the first surface 3 and/or the second surface 4 of the membrane 2, and the fluid is depleted of some amount of complement.

As will be noted in more detail below, in a preferred embodiment, after the biological fluid is collected, at least a portion of the biological fluid will be repeatedly placed in contact with the filter while the biological fluid is stored in the container, and the filter (that can be secured or unsecured in the container) will provide a complement "sink."

Generally, as some of the biological fluid contacts the filter 1, e.g., as the fluid passes tangentially across the surface(s) of membrane 2, at least a portion of the plasma component of the biological fluid passes through the membrane, i.e., the plasma passes from one surface of the membrane and through the central portion to the other surface of the membrane. If desired, the biological fluid is placed in contact with the complement filter without passing the fluid along a substantially defined fluid path through the filter. Illustratively, e.g., the filter 1 can be disposed in the container 10 without directing all of the fluid through the filter membrane 2.

In a preferred embodiment of the invention, the biological fluid is collected or recovered in the container 10, and the biological fluid, or at least one component thereof, is stored in the container. During the storage period, the biological fluid, or at least a portion thereof, repeatedly or continuously contacts the filter 1, and a significant amount of the complement produced during the storage period is retained by the filter. For example, the filter can provide a complement sink that removes and/or retains at least about 50% of the complement (preferably C3a) produced per day. More preferably, the filter removes and/or retains at least about 60% of the complement produced per day. Illustratively, the filter removes and/or retains at least about 60% of the complement from the biological fluid, e.g., a platelet-containing biological fluid, over at least about 48 hours (two days). In some embodiments wherein the stored biological fluid is a platelet-containing fluid such as platelet concentrate (PC), or apheresed platelets, the complement filter removes and/or retains at least about 80%, or even at least about 90%, of the C3a produced per day, for a storage period of 5 days, or more.

In accordance with the invention, the biological fluid, or at least one component thereof, is subsequently passed from the container, e.g., during a transfusion, and the biological fluid is transfused without transfusing a high level of complement.

Preferably, the filter removes complement without significantly removing or significantly adversely affecting the clinical effects of desirable biological fluid components such as plasma, platelets and/or red blood cells. For example, in those embodiments providing for platelet-containing transfusion products, e.g., platelet concentrate, the filter removes complement while allowing a high percentage of the platelets present to be recovered. Typically, the filter allows at least about 80% of the platelets stored in the container to be recovered, e.g., for use in a transfusion. More preferably, the filter allows at least about 85% of these platelets to be recovered. In a more preferred embodiment, the filter allows at least about 90% of the platelets stored in the container to be recovered.

The storage period for the biological fluid will vary depending on the particular biological fluid and/or the intended use, and is known to one of skill in the art. Typically, the storage period is at least several hours, more typically, at least about 24 hours or, e.g., for at least about 48 hours. Illustratively, the storage period can be up to 5 days, or more, for platelet products such as platelet concentrate (PC), platelets prepared from buffy coat, or apheresed platelets, and up to several weeks, or more, for red blood cell-containing products such as packed red cells (PRC) or whole blood.

As noted above, during the storage period, the biological fluid, or at least a portion thereof, repeatedly or continuously contacts the filter 1, and complement is removed (e.g., by binding to the filter). For example, if the container is stored in a substantially upright position, the level of the fluid in the container can be higher than the level of the filter in the container, e.g., to allow the fluid to continually contact the filter. Alternatively, or additionally, the container can be stored in a less upright position, e.g., a substantially horizontal position, thus maintaining fluid/filter contact during the storage period.

In those embodiments wherein the biological fluid is moved during storage (e.g., platelet products should be agitated when stored at 20–24° C.), the movement of the fluid can place the fluid in contact with the filter, and additional complement can be continually removed. Illustratively, moving the fluid includes, but is not limited to, moving the container of fluid from one location to another and/or at least one of centrifuging, inverting, rocking, and rotating, the container.

As noted above, the complement-depleted biological fluid can be passed from the container and transfused. If desired, embodiments of the invention can also include passing the complement-depleted fluid from the container through a blood filter such as a microaggregate filter and/or a leukocyte depletion filter, and transfusing the complement-depleted filtered biological fluid to a patient.

In other embodiments of the invention, the biological fluid is filtered to remove microaggregates and/or leukocytes, before placing the fluid in contact with the complement filter as described above. In another embodiment, a filter assembly comprising a housing having an inlet and an outlet and defining a fluid flow path between the inlet and the outlet includes a complement filter across the fluid flow path. If desired, a filter assembly can include a plurality of filter elements, e.g., to provide complement removal as well as microaggregate and/or leukocyte removal. In some embodiments of a filter assembly including a complement filter across the fluid flow path between the inlet and the outlet, the complement filter has a pore structure that allows desirable cellular components to pass therethrough. For example, in an embodiment, the filter can have a pore rating sufficient to allow platelets to pass therethrough.

In accordance with some embodiments of the invention, the biological fluid, or at least one component thereof, is passed into a container having a complement filter disposed therein, but the fluid or component is not stored in the container. For example, the biological fluid or component(s) can be further processed and passed into other containers (with or without complement filters), and/or transfused without storage.

In accordance with an embodiment of the invention, a complement filter can be placed in a container such as a drip chamber or a bubble trap, and biological fluid contacts the filter as the fluid passes through the container. If desired, the filter can be placed in the container such that all, or nearly all, of the fluid entering the container passes through the filter, e.g., from the first or upstream side of the filter and through the second or downstream side of the filter. In some embodiments wherein nearly all of the fluid passes through the filter, the filter has a pore structure that allows the desirable cellular components to pass therethrough. The complement-depleted biological fluid passing through the drip chamber or bubble trap can then be administered to a patient.

In another embodiment of the invention, the complement filter comprises a non-porous substrate or a substantially non-porous substrate. For example, biological fluid can be placed in contact with a complement filter comprising a substantially non-porous medium that has been surface-modified as described above, and the biological fluid is depleted of at least some amount of complement (e.g., C3a). The complement filter comprising a non-porous substrate or substantially non-porous substrate can be placed in a container (e.g., a flexible container such as a blood bag) as described above.

EXAMPLES

Example 1

The following Example shows that platelets can be stored in a bag containing a complement filter, so that most of the complement produced during storage is retained by the filter. Accordingly, the stored platelets can be directly transfused without transfusing a high level of complement.

A roll of microporous nylon 66 is treated with a solution containing 2% methacrylic acid (MAA), and 2% diethylene glycol dimethacrylate (DEGMA), both in a 40% tertiary butyl alcohol (t-buOH)/60% water solution. The nylon substrate is contacted with the solution and allowed to become completely saturated. The roll of nylon is transferred to and sealed in an irradiation chamber. The irradiation chamber also contains MAA and DEGMA in 40% t-buOH/60% water. The roll is exposed to gamma radiation at a dose rate of 10,000 rads/hour for a total of about 20 hours. After the radiation cycle, the nylon roll is removed from the radiation chamber and placed in contact with a non-woven web and both are rolled together wherein the web is interleaved with the nylon. The interleaved nylon is washed several times with deionized water to remove residual monomer and ungrafted polymer. The nylon is drum dried, and the web is separated from the sheet of nylon membrane.

Six membranes, each having an area of about 5 in$^2$ (about 2.5 in x about 2 in), are cut from the sheet.

The membranes have a CWST of about 82 dynes/cm, a zeta potential of about −20 mV at a pH of about 7 to 7.4, and a pore size of about 0.65 micrometers.

Three membranes are placed in CLX® platelet storage bags (Medsep Corporation, Covina, Calif.), wherein each membrane is arranged in a bag as generally shown in FIG. 4, and wherein two portions of the membrane are secured (e.g., "tack welded"), via radio frequency welding, to one inner surface of the bag. The bags are sealed using radio frequency welding, and then sealed using steam sterilization followed by a heat treatment cycle.

The other three membranes are placed in CLX® bags without securing the membranes to the bags, i.e., the membranes are "free floating". The bags are sealed as described above.

For convenience, the membrane-containing bags will hereinafter be referred to as "complement filter bags", and they contain a "free floating" filter or a "secured" filter.

Six CLX® bags without membranes are provided as controls. These bags will hereinafter be referred to as the "control bags".

After the complement filter bags are produced, platelet-containing fluids are prepared for treatment as follows. Three ABO matched pairs of leukocyte-depleted platelet-rich-plasma (PRP) are pooled, divided into approximately equal volumes, and passed into individual complement filter bags or control bags, while maintaining a closed system. A PRP sample is taken from each unit for testing.

The PRP-containing complement filter bags and control bags are centrifuged to provide platelet-poor-plasma (PPP), as well as a platelet pellet at the bottom of each bag. The PPP is expressed until about 55 grams of PPP is left in each bag, along with the platelet pellet, to provide a unit of platelet concentrate (PC). The bags of PC are left at room temperature for 60 minutes, and then stored on a horizontal shaker in an environmental chamber set at 20–24° C. PC samples are taken from each bag at days 1, 5, and 7, and tested.

Each sample, i.e., the PRP sample (day 0), as well each PC sample (days 1, 5, and 7) is subjected to the following tests: C3a, platelet count (platelet loss), hypotonic shock recovery, shape change, pH, and aggregates (PC only).

The results are as follows: On days 1 and 5, C3a des Arg$^{77}$ is reduced in the free floating complement filter bags, on average, by about 68% and 88%, and reduced in the secured complement filter bags, on average, by about 85% and 81%.

The mean residual C3a des Arg$^{77}$ concentration on day 5 in the free floating complement filter bags and the secured complement filter bags is about 780 ng/ml and about 750 ng/ml respectively. The concentration in the corresponding controls is about 6200 ng/ml, and about 4100 ng/ml, respectively.

The platelet loss in the free floating complement filter bags at day 5 averages about 8%, while that in the secured complement filter bags is about 9%.

With respect to hypotonic shock recovery (% HSR), slightly lower platelet % HSR values are observed in day 1 free floating complement filter bags than are observed in the control bags. No differences occurred in the platelet % HSR between the complement filter bags and the controls for the other storage days.

With respect to extent of shape change (% ESC), slightly lower platelet % ESC values are observed in day 1 and day 5 free floating complement filter bags and day 5 secured complement filter bags, compared to the controls.

All complement bags and control bags maintain a pH greater than 7.3 throughout 5 days of storage.

No differences in aggregates are observed comparing the secured complement filter bags to the respective controls through day 5. The free floating complement filter bags have a few more and larger aggregates at day 5 than do the controls. At day 7 both groups of complement bags generally have more and larger aggregates than the control bags.

This Example shows the complement filters (free floating and secured) remove or prevent C3a from accumulating in stored whole blood derived leukocyte-reduced PC.

Example 2

Membranes are prepared as described above in Example 1.

Six membranes are placed in CLX® bags, wherein each membrane is arranged toward the upper portion of a bag as generally shown in FIG. 3. The membrane is sealed with the top seal of the bag, and at portions 30 and 31 of the bag. The bag also includes additional seals, that do not contact the membrane, at portions 40 and 41. Radio frequency welding is used to provide the seals. The bags are sterilized as described in Example 1.

Six CLX® bags without membranes provide the controls.

After the complement filter bags are produced, platelet-containing fluids are prepared for treatment as follows. Three ABO matched pairs of non-leukocyte-depleted platelet-rich-plasma (PRP) are pooled, divided into approximately equal volumes, and passed into individual complement filter bags or control bags, while maintaining a closed system. A PRP sample is taken from each unit for testing.

The PRP-containing complement filter bags and control bags are processed to provide platelet concentrate (PC), and stored on a shaker, as described in Example 1. PC samples are taken from each bag at days 1, 5, and 7, and tested.

Each sample, i.e., the PRP sample (day 0), as well each PC sample (days 1, 5, and 7) is weighed, and subjected to the following tests: C3a, platelet count (platelet loss), hypotonic shock recovery, shape change, and aggregates (PC only).

The results are as follows: On days 1, 5, and 7, C3a des Arg$^{77}$ is reduced in the complement filter complement bags, on average, by about 88%, 91% and 92%, respectively. The mean residual C3a des Arg$^{77}$ concentration in the complement filter bags on days 1, 5, and 7 is about 150 ng/ml, about 370 ng/ml, and about 590 ng/ml, respectively. The mean residual C3a concentration in the corresponding controls is about 1230 ng/ml, about 4210 ng/ml, and about 7420 ng/ml, respectively.

The mean platelet loss for the complement filter bags at day 5 is about 4%.

With respect to hypotonic shock recovery (% HSR), no apparent differences occur between the complement filter bags and the control bags, except for a slight depression in % HSR in the complement filter bags on day 1.

With respect to extent of shape change (% ESC), slightly lower platelet % ESC values are observed in days 1, 5 and 7 for the control bags as compared to the complement filter bags.

No apparent differences in aggregates are observed comparing the complement filter bags to the respective controls.

This Example shows the complement filters remove or prevent C3a from accumulating in stored whole blood derived non-leukocyte-reduced PC.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A device for treating a biological fluid comprising:
   a flexible container suitable for containing a biological fluid, the container including ports allowing biological fluid in and out of the container; and
   a complement filter, wherein said complement filter is arranged within the container to deplete complement from the biological fluid without passing the biological fluid along a substantially defined fluid flow path through the complement filter.

2. The device of claim 1, wherein at least a portion of the filter is secured to the container.

3. The device of claim 2, wherein a portion of the filter is secured to an inner wall of the container.

4. The device of claim 1, wherein the filter is tethered to the container.

5. The device of claim 1, wherein the filter is not secured to the container.

6. The device of claim 2, wherein a portion of the filter is secured in a side seal of the container.

7. The device of claim 1, wherein the flexible container comprises a blood bag.

8. The device of claim 1, wherein the complement filter comprises a porous polymeric surface-modified membrane having a negative zeta potential at physiological pH.

9. The device of claim 8, wherein the membrane has carboxyl groups bound to the surface of the membrane.

10. The device of claim 1, wherein the complement filter comprises a porous polymeric surface-modified membrane having anionic groups bound to the surface of the membrane.

11. The device of claim 8, wherein the membrane has a pore size of about 2 µm or less.

12. The device of claim 8, wherein the membrane has a pore size of about 1 µm or less.

13. A method for processing a biological fluid comprising:
    storing a platelet-containing biological fluid in a container including a complement filter capable of depleting complement from the biological fluid for a storage period of at least about 24 hours and moving the platelet-containing fluid within the container during at least part of the storage period;
    contacting the complement filter with the platelet-containing biological fluid and
    removing complement from the platelet-containing biological fluid.

14. The method of claim 13, wherein removing complement from the platelet-containing biological fluid includes removing C3a from the fluid.

15. The method of claim 13, including collecting the biological fluid in the container including the complement filter, wherein the complement filter is arranged within the container to contact the biological fluid collected in the container without directing substantially all of the biological fluid through the complement filter as the fluid is collected in the container.

16. The method of claim 14, wherein removing complement from the platelet-containing biological fluid includes removing at least about 60% of C3a from the fluid during a storage period of at least about 24 hours.

17. The method of claim 13, including rocking the container during at least a portion of the storage period.

18. The method of claim 13, wherein the complement filter comprises a porous polymeric surface-modified membrane having a negative zeta potential at physiological pH.

19. The method of claim 13, wherein the platelet-containing biological fluid is a leukocyte-depleted biological fluid.

20. A device for treating a biological fluid comprising:
    a flexible container suitable for containing a biological fluid, the container having inner walls and including ports allowing biological fluid in and out of the container; and
    a complement filter comprising a membrane, wherein the membrane is sealed to an inner wall of the container.

21. The device of claim 20, wherein the flexible container comprises a blood bag.

22. The device of claim 20, wherein the complement filter comprises a porous polymeric surface-modified membrane having a negative zeta potential at physiological pH.

23. The device of claim 21, wherein the membrane has carboxyl groups bound to the surface of the membrane.

24. The device of claim 20, wherein the complement filter comprises a porous polymeric surface-modified membrane having anionic groups bound to the surface of the membrane.

* * * * *